United States Patent [19]

Schröder et al.

[11] Patent Number: 4,702,245

[45] Date of Patent: Oct. 27, 1987

[54] PULSED LASER FOR MEDICAL APPLICATIONS

[75] Inventors: Eckhard Schröder, Eckental; Reinhardt Thyzel, Heroldsberg, both of Fed. Rep. of Germany

[73] Assignee: Meditec-Reinhardt Thyzel GmbH, Heroldsberg, Fed. Rep. of Germany

[21] Appl. No.: 758,662

[22] PCT Filed: Oct. 29, 1984

[86] PCT No.: PCT/DE84/00225

§ 371 Date: Jun. 27, 1985

§ 102(e) Date: Jun. 27, 1985

[87] PCT Pub. No.: WO85/01869

PCT Pub. Date: May 9, 1985

[30] Foreign Application Priority Data

Oct. 29, 1983 [DE] Fed. Rep. of Germany ....... 3339370

[51] Int. Cl.$^4$ .............................................. A61B 17/36
[52] U.S. Cl. .............................. 128/303.1; 128/395; 372/25; 372/31
[58] Field of Search .............................. 372/29, 27, 31; 128/303.1, 395–398; 350/394; 219/121 LA, 121 LB, 121 LZ

[56] References Cited

U.S. PATENT DOCUMENTS

| 3,764,936 | 10/1973 | Baues | 372/30 |
| 4,069,815 | 1/1978 | Lee | 128/683 |
| 4,499,897 | 2/1985 | Roussel | 128/303.1 |
| 4,556,875 | 12/1985 | Ishiwatari | 128/303.1 |
| 4,564,012 | 1/1986 | Shimada et al. | 128/303.1 |
| 4,566,453 | 1/1986 | Kamano et al. | 128/303.1 |
| 4,580,557 | 4/1986 | Hertzmann | 128/303.1 |
| 4,618,958 | 10/1986 | Shibata et al. | 372/29 |

FOREIGN PATENT DOCUMENTS

| 75860 | 9/1982 | European Pat. Off. | 128/303.1 |
| 2493559 | 5/1982 | France | 128/303.1 |
| 2108282A | 5/1983 | United Kingdom . | |

Primary Examiner—Lee S. Cohen
Assistant Examiner—David Shay

[57] ABSTRACT

A pulsed laser for medical application and particularly for ophthalmological treatment is described.

The laser beam pulse has a clearly defined polarization plane. By rotating a polarization splitter cube, it is possible to regulate the energy of the laser beam pulse.

Following each rotation of the polarization splitter cube, and prior to the following treatment pulse, a control system releases a test pulse. The energy of the test pulse is measured while the shutter closes the treatment beam path.

According to a preferred embodiment, the laser is a neodymium-YAG laser.

6 Claims, 1 Drawing Figure

PULSED LASER FOR MEDICAL APPLICATIONS

TECHNICAL FIELD

The invention relates to a pulsed laser for medical applications, and in particular for ophthalmological treatment purposes.

Neodymium-YAG lasers with mode locking or Q-switching can be used as pulsed lasers. It is also possible to use other pulsed lasers, such as argon lasers.

BACKGROUND ART

Pulsed lasers are used for operations on the human eye. In the case of the known lasers, there is no control of the laser pulse energy prior to the release of the operating pulse. It is readily apparent that if the laser pulse energy is too high, the eye to be treated can be seriously damaged.

DISCLOSURE OF THE INVENTION

The object of the present invention is to provide a pulsed laser for medical applications and in particular for ophthalmological treatment purposes, in which the energy of the laser pulses can be controlled.

According to the invention this object is solved by regulating the energy of the laser beam pulse, having a clearly defined polarization plane, by rotating a polarization splitter cube and by having a control system release a test pulse after each rotation of the polarization splitter cube. A light-sensitive element measures the energy of the test pulse. The treatment beam path is shut off by a shutter during the test pulse.

The invention makes use of a laser, whose laser beam pulse has a clearly defined polarization plane and in which the energy of a single pulse can be controlled by rotating a polarization splitter cube. As has been recognized by the invention, in the case of such lasers the following causes for incorrect energy release exist:

1. As a result of mechanical errors and faults, the polarization splitter cube is not in its correct desired position, so that it does not permit the passage of the desired laser energy fraction.

2. The energy released by the laser during a pulse does not correspond to the desired energy.

By means of the invention it is now possible that the energy of the two successive laser pulses for lasers used in ophthalmic treatment never fluctuates by more than ±20%. Such divergences of the actual energy from the desired energy are acceptable in medical applications and particularly in operations on the human eye.

Thus, no matter which of the two above causes for an incorrect energy release exists, a treatment pulse energy differing in an excessive manner from the desired energy can be detected in that following each rotation of the polarization splitter cube, and prior to the following treatment pulse, a test pulse is released. In order that the test pulse cannot injure a patient or the operator, the test pulse is released internally, i.e. within the laser equipment, because during the release of the test pulse, a shutter shuts off the outwardly directed beam path.

In advantageous further developments of the invention the output signal of the light-sensitive element is used for regulating the energy of the laser pulses and the automatic setting of the rotation angle of the polarization splitter cube. The output signal may also regulate the voltage of the laser flash lamp. The control system may be used to rotate the polarization splitter cube into a position in which it permits the passage of the minimum laser energy when the laser is switched on. The polarization splitter cube may be rotated by an operator by means of a knob with the test pulse being automatically released by the control system when the knob is released. A beam splitter may be arranged in a fixed manner in the laser beam path so as to deflect part of the beam on to the light-sensitive element.

The invention can be used with particular advantage in the case of neodymium-YAG lasers, which are often used for operations on the human eye. As a function of the type of control (passive mode locking or active/passive Q-switching), the energy of such lasers can fluctuate in the aforementioned range. Through the release of a "test shot" or optionally several test pulses prior to the following treatment pulse, it is possible to reliably narrow down the range within which the energy can fluctuate.

The measured energy signal for the laser pulse is available for regulating the laser energy.

This energy regulation can be brought about by regulating the rotation angle of the polarization splitter cube or the voltage of the laser flash lamp. For example, regulation can take place with an electronic control unit, which can be constructed without difficulty by the average professional.

Advantageous further developments of the invention increase the operational reliability of the laser.

In one embodiment, after the laser is switched on, the control system rotates the polarization splitter cube into the position in which it permits the passage of the minimum laser energy. The automatic "zero position" of the polarization splitter cube after switching on the laser forces the operator to constantly reset the laser energy required for a particular treatment. This avoids, on the one hand, an excessively high energy set for a previous treatment being used again without further consideration. It also permits simplification of the control of the equipment, because the polarization splitter cube is always rotated prior to a treatment pulse, so that a test pulse can only be released by a rotation of said cube.

It is particularly advantageous if the test pulse is always released automatically by the control system on releasing the button or knob provided for the mechanical rotation of the polarization splitter cube. Particularly in the case of treatments to the eyes, the time lag between the release of the test pulse and the release of the treatment pulse must be very short, because, e.g. by means of a slit lamp, the operator checks the position of the eye and releases the treatment pulse at the instant when the eye is in the correct position. It would be disadvantageous if it were necessary to release a "test shot" prior to the treatment pulse.

In another embodiment the beam splitter is always present in a fixed position in the beam path, preventing any influencing of the laser energy through the pivoting in and out of the beam splitter.

BRIEF DESCRIPTION OF THE DRAWINGS

The figure is a plan view of the apparatus of the present invention.

BEST MODE FOR CARRYING OUT THE INVENTION

Figure 1:
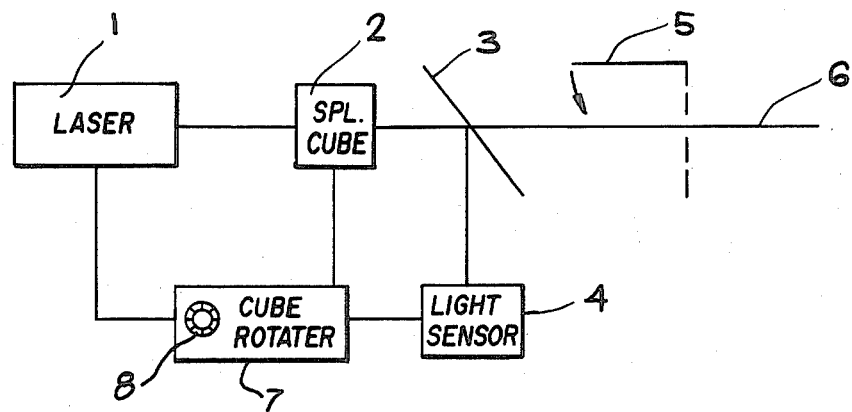

With reference to the figure the laser according to the invention has a laser tube 1, a polarization splitter cube 2, a beam splitter 3 and a light-sensitive element 4, together with a shutter 5.

The laser tube 1 can be a neodymium-YAG laser, into which is already integrated a polarizer, so that the laser tube 1 emits a polarized laser beam pulse with a clearly defined polarization plane. Thus, through mechanical rotation of the polarization splitter cube 2, it is possible to adjust the energy passing through said cube.

The polarization splitter cube can be mechanically rotated by means of a knob or button 8. On releasing the latter, a test pulse is automatically released, shutter 5 shutting the treatment beam path 6.

If the measured energy within a given tolerance range, e.g. within ±20% of the given desired value in the case of a neodymium-YAG laser for medical purposes, the operator can release a treatment pulse. If this condition is not fulfilled, the release of a treatment pulse is prevented. It is also possible to use the test measurements for regulating the laser energy by regulating the flash lamp voltage.

In the embodiment shown in the figure, the beam splitter 3, which deflects part of the laser beam on to the light-sensitive element 4, still remains in the treatment beam path if no test pulse is released. In this way the treatment beam path is not modified on releasing a treatment pulse compared with the beam path on releasing a test pulse, and the operational reliability is further increased. It is also possible to provide the light-sensitive element, on shutter 5, so that there is no need for a beam splitter for deflecting part of the laser beam.

The control system 7 can be one of any constructed electronic circuit. The control system can have a microcomputer, which releases a test pulse on releasing the knob 8 for the polarization splitter cube, measures the energy of the pulse in the aforementioned way, and optionally correspondingly regulates the laser tube energy, by rotation of the polarization splitter cube 2 and by regulation of the voltage of the lase flash lamp.

We claim:

1. A safety system for treatment lasers comprising,
   a pulsed laser emitting a series of beam pulses aimed along a laser beam path at a target,
   a polarization splitter cube rotatably fixed in said laser beam path, said beam pulses along said beam path having a defined polarization plane and having an energy regulated by rotation of said polarization splitter cube,
   a beam splitter arranged in a fixed manner in said beam path beyond said polarization splitter cube, said beam splitter deflecting at least a portion of the beam pulses,
   a light-sensitive element disposed to receive said portion of beam pulses deflected by said beam splitter,
   a control means for controlling the rotation of said polarization splitter cube and for initializing beam pulses, including treatment pulses and test pulses, said treatment pulses having a first beam energy, said control means initializing at least one test pulse in time relation to said treatment pulses, said test pulse having a second beam energy, said control means being in communication with said light-sensitive element for determination of beam energy, said control means connected to provide rotation to said polarization splitter cube reducing an error amount when said second beam energy represents a desired output beam pulse energy plus an error amount, said control means automatically rotating said polarization splitter cube into a position which establishes the passage of minimum laser energy upon initial activation of said laser, and
   shutter means disposed in said beam path for automatically blocking said test pulses from the target, said shutter means permitting said treatment pulses to travel to the target.

2. The system of claim 1 wherein said control means includes a signal loop connected from the light-sensitive element to the rotatable polarization splitter cube whereby said signal loop carries error signals used to reduce said error amount.

3. The system of claim 1 wherein said control means includes a signal loop connected from said light-sensitive element to a variable laser excitation source whereby said signal loop carries error signals used to reduce said error amount by varying laser excitation.

4. The system of claim 1 wherein said rotatable polarization splitter cube includes a manually operable control for rotation of said polarization splitter cube by an operator, said control having means for automatically initiating a test pulse upon release of said manually operable control.

5. The system of claim 4 wherein said manually operable control includes a knob.

6. A safety system for treatment lasers comprising,
   a pulsed laser emitting a series of beam pulses aimed along a laser beam path at a target,
   a polarization splitter cube rotatably fixed in said laser beam path, said beam pulses along said beam path having a clearly defined polarization plane and having an energy regulated by rotation of said polarization splitter cube,
   a beam splitter arranged in a fixed manner in said beam path beyond said polarization splitter cube, said beam splitter deflecting at least a portion of the beam pulses,
   a light-sensitive element disposed to receive said portion of beam pulses deflected by said beam splitter,
   a control means coupled to the splitter cube for controlling the rotation of said polarization splitter cube to produce first and second beam energy levels, corresponding respectively to treatment and test levels, said control means being in communication with said light-sensitive element for determination of beam energy, said control means connected to provide rotation to said polarization splitter cube reducing an error amount when said second beam energy level represents a desired output beam pulse energy plus an error amount, said control means automatically rotating said polarization splitter cube into a position which establishes the passage of a relatively low laser beam energy in comparison to the beam first and second energy levels, upon initial activation of said laser,
   a manually operable knob means for rotation of said polarization splitter cube by an operator, and for automatically initiating a test pulse upon release of said manually operable knob means, and
   shutter means disposed in said beam path for automatically blocking said test pulses from the target, yet permitting said treatment pulses to travel to the target.

* * * * *